United States Patent [19]

Matsuo et al.

[11] Patent Number: 4,657,891
[45] Date of Patent: Apr. 14, 1987

[54] DIURETIC PEPTIDE, AND PRODUCTION AND USE THEREOF

[75] Inventors: Hisayuki Matsuo, 6653, Ooaza-Kihara, Kiyotake-cho, Miyazaki-gun, Miyazaki-ken; Kenji Kangawa, Miyazaki, both of Japan

[73] Assignees: Suntory Limited, Osaka; Hisayuki Matsuo, both of Japan

[21] Appl. No.: 706,381

[22] Filed: Feb. 27, 1985

[30] Foreign Application Priority Data

Mar. 2, 1984 [JP] Japan .................................. 59-38816

[51] Int. Cl.$^4$ ........................ A61K 37/24; C07K 7/10
[52] U.S. Cl. ...................................... 514/11; 530/324
[58] Field of Search ................... 260/112.5 R; 514/11; 530/324

[56] References Cited

U.S. PATENT DOCUMENTS

4,496,544  1/1985  Needleman .................. 260/112.5 R
4,508,712  4/1985  Needleman ........................... 514/11

OTHER PUBLICATIONS

Febs 1268, vol. 167, No. 2, (1984) 352–357.
Jamieson, J. D. and Palade, G. E., "Specific Granules in Atrial Muscle Cells", The Journal of Cell Biology, vol. 23 (1964) pp. 151–172.
de Bold, A. J. et al, "A Rapid and Potent Natriuretic Response to Intravenous Injection of Atrial Myocardial Extract in Rats", Life Sciences, vol. 28 (1981) pp. 89–94.
Keeler, R., "Atrial Natrieuretic Factor has a Direct, Prosteglan-Independent Action on Kidneys", Can. J. Physiol. Pharmacol., vol. 60 (1982) pp. 1078–1082.
Currie, M. G. et al, "Bioactive Cardiac Substances: Potent Vasorelaxant Activity in Mammalian Atria", Science, vol. 221 (1983) pp. 71–73.
Flynn, T. G. et al, "The Amino Acid Sequence of an Atrial Peptide with Potent Diuretic and Natriuretic Properties", Biochemical and Biophysical Research . . .

Kangawa, K. and Matsuo, H., "Purification and Complete Amino Acid Sequence of α-Human Atrial Natriuretic Polypeptide (α-haNP)", Biochemical and Biophysical . . . .

*Primary Examiner*—Delbert R. Phillips
*Attorney, Agent, or Firm*—Burns, Doane, Swecker & Mathis

[57] ABSTRACT

There are disclosed a new peptide β-rANP of the following structure:

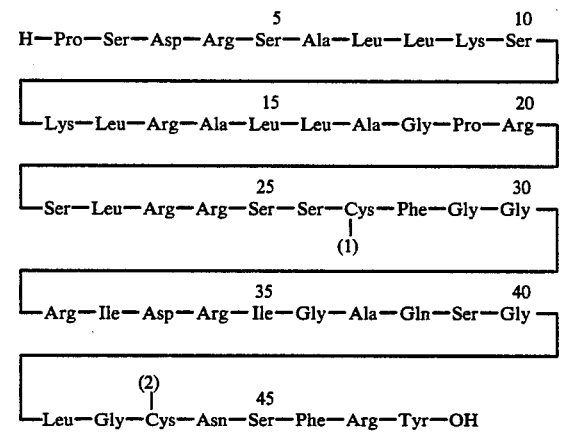

and acid addition salt thereof; a diuretic composition and a hypotensor composition containing the β-rANP or an acid addition salt thereof; and processes for the production thereof.

13 Claims, 4 Drawing Figures

DIURETIC PEPTIDE, AND PRODUCTION AND USE THEREOF

BACKGROUND OF THE INVENTION

1. Field of the Invention

The present invention relates to a novel peptide, a process for the production thereof, and a pharmaceutical composition containing the novel peptide as a diuretic or hypotensor.

2. Description of the Related Art

A normal regulation of the blood pressure in a human body is important for the maintenance of personal health, and various physical and humoral factors contribute to this regulation of the blood vessels, etc. The humoral factors include, for example, the renin-angiotensin-aldosterone system, catecholamines, prostaglandins, kinin-kallikrein system, and natriuretic hormones including ouabain-like substances. Herein the term "natriuretic" will denote selective excretion of sodium cation relating to potassium cation.

Granules morphologically similar to granules present in peptide hormone-producing cells are found in human atrium (J. D. Jamieson and G. E. Palade, *J. Cell Biol.*, 23, 151, 1964). A homogenate of rat atrium and granules contained therein are known to show natriuretic action in rats (A. J. DeBold et. al., *Life Science*, 28, 89, 1981; R. Keeller, *Can. J. Physiol. Pharmacol.*, 60, 1078, 1982). Recently G. Currie et. al. suggested peptide-like substances with a molecular weight of 20,000 to 30,000, or not more than 10,000, present in atrium of humans, rabbits, swine, and rats, and having natriuretic action (*Science*, 221, 71–73, 1983).

Moreover, a peptide consisting of 28 amino acids derived from rat atrium cordis was identified (*Biochem. Biophys. Res. Commun.;* vol 117, No. 3, p 859–865, 1983). The present inventors found a new peptide consisting of 28 amino acids from human atrium cordis; referred to as "α-human artrial natriuretic polypeptide" and abbreviated as "α-hANP" (*Biochem. Biophys. Res. Commun.* Vol 118, No. 1, p 131–139, 1984).

SUMMARY OF THE INVENTION

The present invention provides a new peptide having natriuretic action and hypotensive or antihypertensive action. The peptide according to the present invention is hereinafter referred to as "β-rat atrial natriuretic polypeptide" and abbreviated as "β-rANP".

There is also provided a process for production of the peptide.

Another object of the present invention is to provide a pharmaceutical composition containing the peptide as a diuretic or hypotensor.

Other objects and advantages of the present invention will be apparent from the description set forth hereinbelow.

DESCRIPTION OF THE PREFERRED EMBODIMENT

Figure 1:
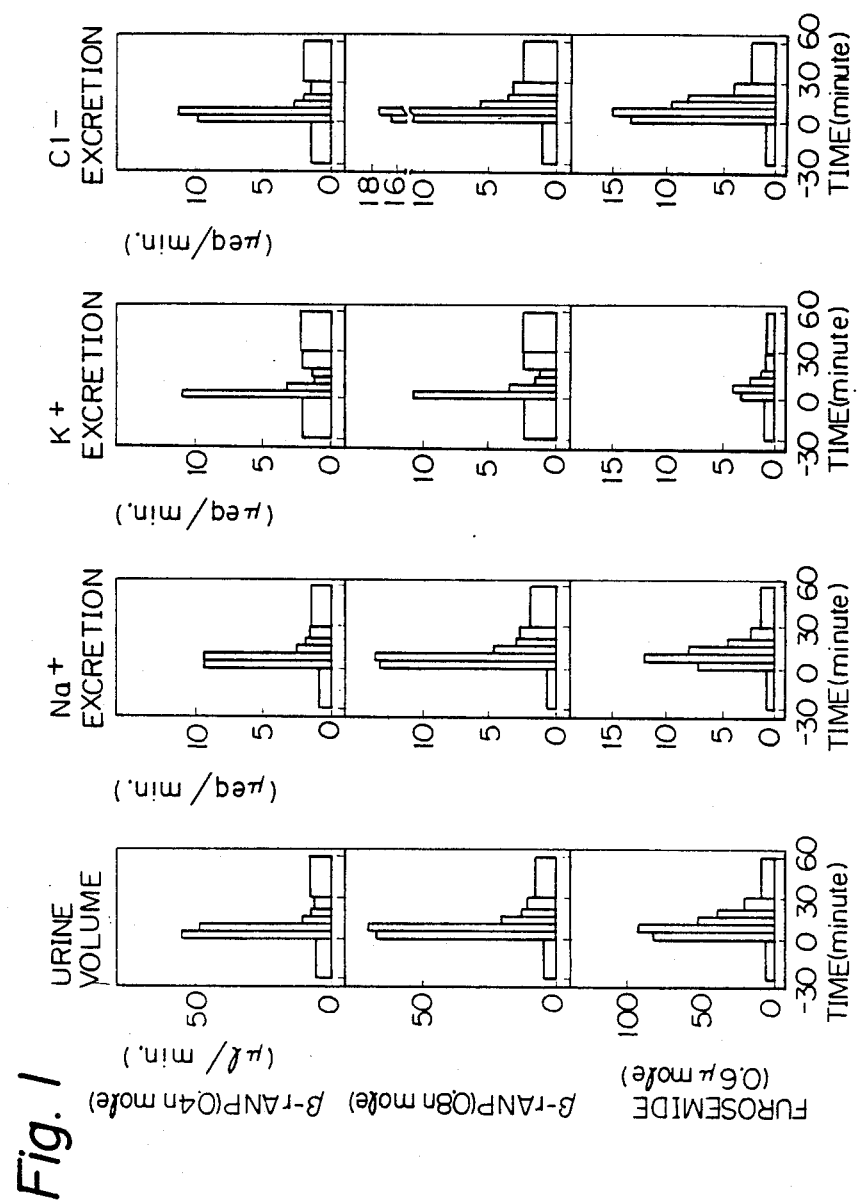
FIG. 1 contains graphs comparing the diuretic action of the β-rANP and furosemide.

At present, furosemide as a natriuretic agent is used for the treatment of essential hypertension. However, the structure of the furosemide is different to that of the new peptide according to the present invention.

The present inventors isolated a peptide, in substantially pure form, consisting of 48 amino acid residues and having a molecular weight of about 5,000, determined the structure of the peptide and found that the peptide showed notable diuretic, natriuretic, and hypotensive actions and chick rectum relaxation activity.

Structure and Physico-chemical Properties of the β-rANP (1) Structure

The β-rANP has the following structure:

```
         5                    10
H—Pro—Ser—Asp—Arg—Ser—Ala—Leu—Leu—Lys—Ser—┐
                                            │
         15                   20            │
┌—Lys—Leu—Arg—Ala—Leu—Leu—Ala—Gly—Pro—Arg—┘
│
│        25                   30
└—Ser—Leu—Arg—Arg—Ser—Ser—Cys—Phe—Gly—Gly—┐
                             │             │
                            (1)            │
                                           │
         35                   40           │
┌—Arg—Ile—Asp—Arg—Ile—Gly—Ala—Gln—Ser—Gly—┘
│
│       (2)
│        │          45
└—Leu—Gly—Cys—Asn—Ser—Phe—Arg—Tyr—OH
``` wherein (1) and (2) are bonded through a disulfide bond formed by two sulfur atoms of two cysteines, Pro represents L-proline, Ser represents L-serine, Asp represents L-aspartic acid, Arg represents L-arginine, Ala represents L-alanine, Leu represents L-leucine, Lys represents L-lysine, Gly represents glycine, Cys represents L-cysteine, Phe represents L-phenylalanine, Ile represents L-isoleucine, Gln represents L-glutamine, Asn represents L-asparagine, and Tyr represents L-tyrosine, and wherein the amino acid chain has an amino-terminal at the left end and carboxy-terminal at the right end.

(2) Molecular weight: about 5,000 as determined by gel-filtration (5194.09 as calculated).

(3) UV spectrum: Max=275 mm.

(4) Color reactions: Ehrlich's reaction, negative; Sakaguchi's reaction, positive; Pauly's reaction, positive.

(5) Distinction of basic, acidic, or neutral property: basic.

(6) Solubility in solvents: soluble in water, partially in methanol, and acetic acid; insoluble in ethyl acetate, butyl acetate, ethyl ether, hexane, petroleum ether, benzene, and chloroform.

(7) Amino acid composition by amino acid analysis:

An aliquot of β-rANP was reduced with dithiothreitol and carboxymethylated with 2-iodo acetic acid to prepare RCM-β-rANP. An aliquot of the RCM-β-rANP was digested with trypsin to prepare 11 fragments (T-1 to T-11). The native β-rANP, the RCM-β-rANP and the fragments were subjected to amino acid analysis after hydrolysis with 6N hydrochloric acid for 24 hours.

The amino acid composition of the β-rANP, RCM-β-rANP and fragments, and the position of the fragments in the amino acid sequence of β-rANP is shown in the following Table 1.

artery for measurement of the blood pressure, and a venous cannula was inserted into a femoral vein for the administration of Ringer's solution. 1.2 ml of Ringer's solution was infused at a flow rate of 1.2 ml/hour.

A bladder cannula made of silastic tube with a inner diameter of 0.02 inches and an outer diameter of 0.037 inches was inserted into the bladder, and via the cannula, a urine sample was collected into a test tube. The

TABLE 1

| Amino acid | β-rANP | RCM-β-rANP | \multicolumn{11}{l}{Fragment derived from digestion of RCM-β-rANP with trypsin} |
|---|---|---|---|---|---|---|---|---|---|---|---|---|---|
| | | | T-1 | T-2 | T-3 | T-4 | T-5 | T-6 | T-7 | T-8 | T-9 | T-10 | T-11 |
| CmCys* | | 1.96(2) | | | | | | | 0.86 (1) | | | 1.00 (1) | 1.07 (1) |
| Asp | 3.10(3) | 3.02(3) | 1.04 (1) | | | 1.04 (1) | | | | | | 0.98 (1) | 1.05 (1) |
| Ser | 7.87(8) | 7.87(8) | 1.09 (1) | | | | 1.12 (1) | 1.04 (1) | 1.90 (2) | 1.11 (1) | | 2.05 (2) | 2.06 (2) |
| Glu | 1.02(1) | 1.00(1) | | | | | | | | | | 0.93 (1) | 0.95 (1) |
| Pro | 2.17(2) | 2.06(2) | 1.08 (1) | | | | | | | | 1.03 (1) | | |
| Gly | 6.07(6) | 5.90(6) | | | | | | | 1.81 (2) | | 0.95 (1) | 2.84 (3) | 2.82 (3) |
| Ala | 4.07(4) | 3.95(4) | | | | | | | | 1.02 (1) | 1.84 (2) | 0.96 (1) | 1.05 (1) |
| Leu | 7.25(7) | 7.03(7) | | | 0.99 (1) | | 1.02 (1) | 0.99 (1) | | 2.00 (2) | 1.88 (2) | 0.97 (1) | 0.93 (1) |
| Tyr | 1.00(1) | 1.00(1) | | 1.00 (1) | | | | | | | | | 0.95 (1) |
| Phe | 1.94(2) | 2.07(2) | | | | | | | 0.94 (1) | | | 0.94 (1) | 0.94 (1) |
| Lys | 2.01(2) | 2.04(2) | | | | | | | | 1.13 (1) | | | |
| Arg | 8.26(8) | 7.79(8) | 1.00 (1) | | 1.00 (1) | 1.00 (1) | 1.00 (1) | 2.00 (2) | 1.00 (1) | | 1.00 (1) | 1.00 (1) | 1.00 (1) |
| Total | (48) | (48) | (4) | (1) | (2) | (3) | (3) | (4) | (7) | (5) | (7) | (13) | (14) |
| Position | | | 1–4 | 48 | 12–13 | 32–34 | 21–23 | 21–24 | 25–31 | 5–9 | 14–20 | 35–47 | 35–48 |

Value in parentheses represents theoretical mole ratio.
CmCys means carboxymethyl cysteine.
(Cys)$_2$ means cystine.

(8) Formation of salts: the β-rANP is a basic compound as described in item (5), and can form acid addition salts with an inorganic acid such as hydrochloric acid, sulfuric acid, phosphoric acid, or an organic acid such as formic acid, acetic acid, propionic acid, succinic acid, and citric acid.

Physiological Properties of β-rANP

The β-rANP according to the present invention has notable diuretic, natriuretic, and hypotensive or antihypertensive actions.

Test method:

Male rats weighing 300 to 400 grams were anesthetized by intraperitoneal administration of pentobarbital at a dosage of 60 mg/kg, and used for tests of the β-rANP according to the method described in *Life Sciences*, Vol. 28, pp 89–94.

To keep the respiratory tract open, a tracheal cannula (PE-240 Clay-Adams) was inserted into the trachea. An arterial cannula (PE-50) was inserted into a femoral collection of urine was carried out for 30 minutes before administration of the test compound, and every five minutes after the administration.

A predetermined amount of the test compound β-rANP was dissolved in 50 μl of sterilized physiological saline with 5 μg of bacitracin, and the solution was injected into the jugular vein.

The amount of β-rANP administered was 0.4 n mole (group II), or 0.8 n mole (group III). The control group (group I) was administered 50 μl of physiological saline containing only bacitracin. For comparison, group IV received 50 μl of physiological saline containing bacitracin and 1.21μ mole of furosemide, which is a known natriuretic agent.

Groups I to III each consisted of three animals, and group IV consisted of four animals.

Test results:

The results of the test are set forth in the following Table 2.

TABLE 2

| | Control I | β-rANP 0.4 n mole II | β-rANP 0.8 n mole III | Furosemide 1.21 μmole IV |
|---|---|---|---|---|
| Urine volume B[3] (μl/min) A[4] | 5.8 ± 0.3 10.9 ± 2.2 | 5.98 ± 1.61 55.8 ± 3.4 | 4.97 ± 0.85 68.2 ± 30.1 | 8.6 ± 1.9 167 ± 28 |
| Na$^+$ Excretion (n eq/min) | 618 ± 111 1020 ± 166 | 967 ± 301 9584 ± 795 | 749 ± 100 13539 ± 5582 | 1134 ± 283 20018 ± 2990 |
| K$^+$ Excretion (n eq/min) | 2213 ± 348 3661 ± 670 | 2154 ± 322 11269 ± 1254 | 2409 ± 296 10825 ± 4099 | 1945 ± 465 6897 ± 392 |
| Cl$^-$ Excretion (n eq/min) | 539 ± 65 1247 ± 434 | 1532 ± 680 9972 ± 1756 | 1283 ± 117 16597 ± 6107 | 1708 ± 334 40242 ± 6859 |

TABLE 2-continued

|  | Control I | β-rANP 0.4 n mole II | β-rANP 0.8 n mole III | Furosemide 1.21 μmole IV |
| --- | --- | --- | --- | --- |
| Na/K ratio | 0.28 | 0.45 | 0.31 | 0.58 |
|  | 0.28 | 0.85 | 1.25 | 2.90 |
| Number of animals | 3 | 3 | 3 | 4 |

[1]All animals received 5 μg bacitracin.
[2]Values are average for 3 or 4 animals.
[3]B is value for sample collected 30 minutes before administration of test compound.
[4]A is value for sample collected 5 minutes after administration of test compound.

As shown in Table 2, β-rANP shows notable diuretic and natriuretic actions. Namely, 0.8 n mole of β-rANP injected into the jugular vein of a rat provides diuretic and natriuretic action comparable to those provided by 1.21μ mole of furosemide, which is a known diuretic agent. 0.8 n mole of β-rANP gives about a 14-fold increase in the urination volume, and about a 18-fold increase in the sodium excretion. When β-rANP is not administrated, the Na/K ratio in urine is about 0.3, but when 0.8 n mole of β-rANP is administrated, this ratio rises to about 1.25, revealing that β-rANP is useful as a natriuretic agent.

FIG. 1 shows comparisons between β-rANP and furosemide regarding changes in the urination volume, and the excretions of sodium cation, potassium cation, and chlorine anion after the administration of β-rANP or furosemide. As shown in the Figure, β-rANP causes diuretic and natriuretic actions more rapidly than furosemide.

Another test was carried out according to the above-mentioned test method except that 0.4 n mole or 0.8 n mole of β-rANP, 0.4 n mole of α-human atrial natriuretic polypeptide (α-hANP), or 0.3μ mole of furosemide were administrated to each group consisting of three animals, and relative amounts of urine, sodium, and potassium cations and chloride anion of samples obtained for 30 minutes before and after the administration were measured.

The results are set forth in Table 3, wherein the percentage of the amount after the administration relating to the amount before the administration is shown.

TABLE 3

| Test compound | Urine volume | Na+ Excretion | K+ Excretion | Cl− Excretion |
| --- | --- | --- | --- | --- |
| β-rANP (0.4 n mol) | 562 ± 155 | 663 ± 151 | 162 ± 23 | 524 ± 147 |
| β-rANP (0.8 n mol) | 667 ± 29 | 911 ± 119 | 158 ± 15 | 662 ± 38 |
| α-hANP (0.4 n mol) | 557 ± 104 | 911 ± 154 | 138 ± 7 | 872 ± 112 |
| Furosemide (0.3 μmol) | 497 ± 165 | 470 ± 154 | 119 ± 13 | 440 ± 129 |

Values are average for 3 animals.

As shown in Table 3, the activities of β-rANP are comparable to those of α-hANP and about a 1000 times greater than furosemide on the mole base.

Use of β-rANP as a pharmaceutical product

Repeated administration of β-rANP does not stimulate production of antibodies, and does not cause anaphylaxis shock. β-rANP consisting of L-amino acids is gradually hydrolized in a body providing the L-amino acids, and therefore shows little toxicity.

Due to the higher diuretic, natriuretic, and blood pressure-lowering or antihypertensive actions, and the lower toxicity, β-rANP is useful as an active ingredient for pharmaceutical compositions such as a diuretic and a hypotensor. β-rANP is administered at 0.1 μg/kg to 1 mg/kg, preferably 1 μg/kg to 100 μg/kg.

β-rANP can be administered in the same manner as conventional peptide type pharmaceuticals. Namely, β-rANP is preferably administered parenterally, for example, intravenously, intramuscularly, intraperitoneally, or subcutaneously. β-rANP, when administered orally, may be proteolytically hydrolyzed. Therefore, oral application is not usually effective. However, β-rANP can be administered orally as a formulation wherein β-rANP is not easily hydrolyzed in a digestive tract, such as liposome-microcapsules. β-rANP may be also administered in suppositories, sublingual tablets, or intranasal spray.

The parenterally administered pharmaceutical composition is an aqueous solution containing about 0.000005 to 5%, preferably 0.00005 to 0.5% of β-rANP, which may contain, in addition to β-rANP as an active ingredient, for example, buffers such as phosphate, acetate, etc., osmotic pressure-adjusting agents such as sodium chloride, sucrose, and sorbitol, etc., antioxidative or antioxygenic agents, such as ascorbic acid or tochopherol and preservatives, such as antibiotics. The parenterally administered composition also may be a solution readily usable or in a lyophilized form which is dissolved in sterile water before administration.

Production of β-rANP

β-rANP can be produced by either the extraction of the β-rANP from rat atrium or by chemical synthesis.

In the former process, rat atrium is homogenized in an acidic aqueous solution such as a phosphate buffer solution, or an acetic acid solution. Subsequently, β-rANP is purified according to a conventional method suitable for the purification of peptide, such as centrifugation, isoelectric point precipitation, solvent extraction, ultrafiltration, gel filtration, adsorption chromatography or high performance liquid chromatography (HPLC), or a combination of such methods. In the above-mentioned methods, chick rectum relaxation activity is conveniently used to select fractions containing β-rANP, because β-rANP has this activity. In the chromatography methods, the β-rANP containing fractions can be also selected by molecular weight (about 5,000). Chemical synthesis is preferable for the industrial production of β-rANP, in which chemical synthesis, a liquid phase method or solid phase method, or a combination thereof can be used. The solid phase method such as Merrifield's method [R. B. Merrifield, J. Am. Chem. Soc. 85, 2184 (1963)] is most convenient.

In Merrifield's method, each amino acid is protected preferably with tert-butyloxycarbonyl (Boc) at the α-amino group; a hydroxyl group in tyrosine is protected preferably with 2,6-dichlorobenzyl group ($Cl_2Bzl$); a guanidino group in arginine is protected preferably with a tosyl group (Tos); a hydroxyl group in serine is protected preferably with a benzyl group (Bzl); a β-carboxyl group in aspartic acid is protected preferably with an O-benzyl group (O-Bzl); and a thiol group in cysteine is protected preferably with an acetoamidomethyl group (Acm). In the Merrifield method, first a protected derivative of C-terminal amino acid L-tyrosin, i.e., Boc-Tyr ($Cl_2Bzl$) is introduced onto a solid phase resin carrier, such as chloromethyl-resin, and subsequently, each suitably protected amino acid is coupled to a terminal amino acid of an intermediate amino acid chain bonded to the resin, in the order of the amino acid sequence of β-rANP. After all the amino acids are coupled in the predetermined order, the protected β-rANP thus obtained is removed from the resin by treatment with hydrogen fluoride, and simultaneously protecting groups other than Acm are also removed. The product is then reduced to obtain $Cys^{27,43}$ (Acm)-β-rANP), which is then oxidized with iodine to remove the thiolprotecting group Acm, and simultaneously, to form a disulfide bond. The crude β-rANP thus obtained is then purified by conventional methods such as gel filtration, reverse phase HPLC, etc., to obtain purified β-rANP.

EXAMPLES

The present invention will now be further illustrated by, but is by no means limited to, the following examples.

EXAMPLE 1

Preparation of β-rANP from rat atrium cordis

Soon after death, 525 g of rat atrium cordis from 258 rats was removed and boiled in ten volumes of 1M acetic acid aqueous solution for ten minutes, to inactivate protease present in the atrium cordis. The boiled atrium cordis in the acetic acid solution was then cooled to 4° C., and homogenized with a Polytron homogenizer to extract the β-rANP. The homogenate thus obtained was centrifuged at 12000×G for 30 minutes to obtain 420 ml of a supernatant. The supernatant thus obtained was subjected to ultrafiltration using an ultrafilter (Amicon UM-2) to obtain 50 ml of a desalted and concentrated solution.

To the solution, acetone was dropwide added in an amount of 66% of the final concentration to precipitate impurities. The mixture thus obtained was then evaporated to dryness. The residue thus obtained was dissolved in 100 ml of 1 N acetic acid.

The solution was applied on SP-Sephadex C-25 column (Pharmacia, 1.5×17.5 cm) equilibrated with 1M acetic acid solution. The elution was carried out with 1N acetic acid, 2N pyridine solution, and 2N pyridine-1N acetic acid solution (pH 5.0), in that order, to obtain fractions SP-I, SP-II, and SP-III. The fraction SP-III was lyophilized to obtain 113 mg of lyophylizate, which was then dissolved in 1N acetic acid.

Figure 2:
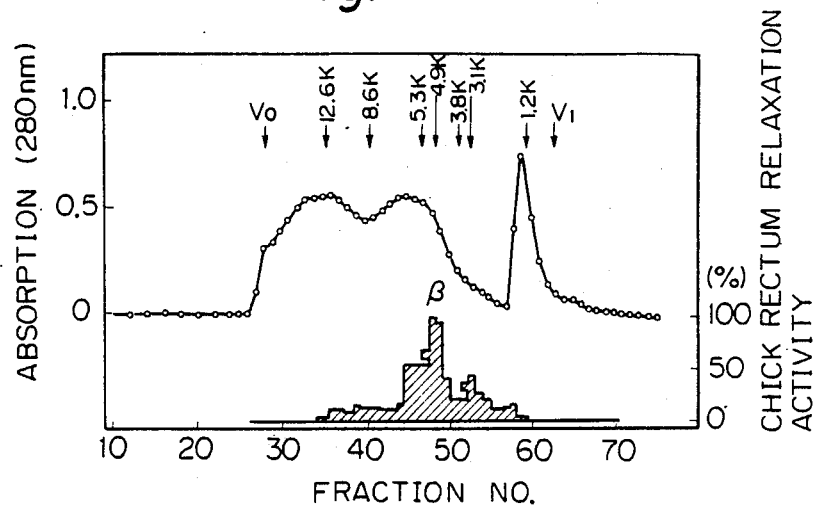
FIG. 2 is a chromatogram showing an elution profile wherein the β-component is separated from the other components by gel filtration with SP-Sephadex G-25 during isolation of the β-rANP from rat atrium.

The solution thus obtained was gel-filtrated with Sephadex G-25 column (1.8×135 cm) at a flow rate of 10.2 ml/hour, collecting 5 ml of fractions. Thereby, β fractions (fractions No. 42 to 51, molecular weight about 5,000) which have chick rectum relaxation activity were obtained. The elution profile is shown in FIG. 2. The β fractions (No. 42 to 51) were combined for further purification.

Figure 3:
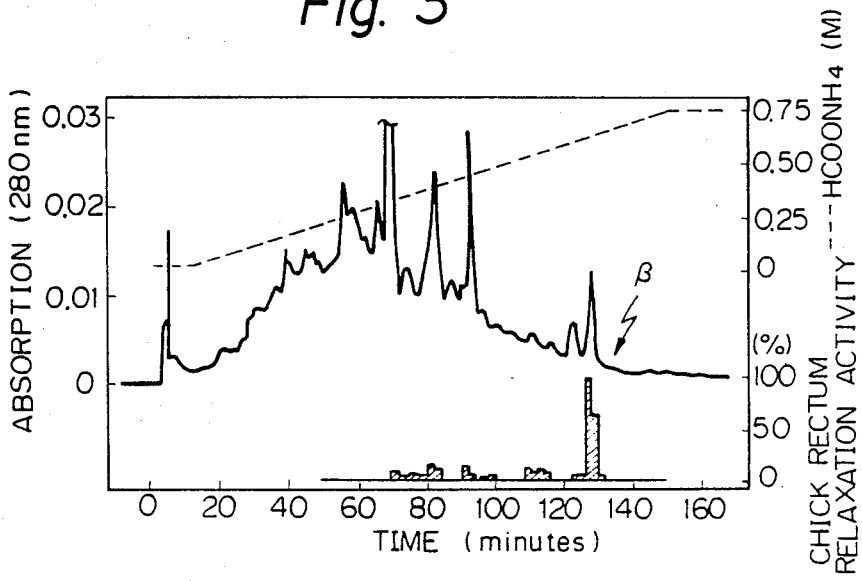
FIG. 3 is a chart showing an elution profile wherein β-rANP is purified by high performance liquified chromatography (HPLC) with TSK-CM2SW column.
Figure 4:
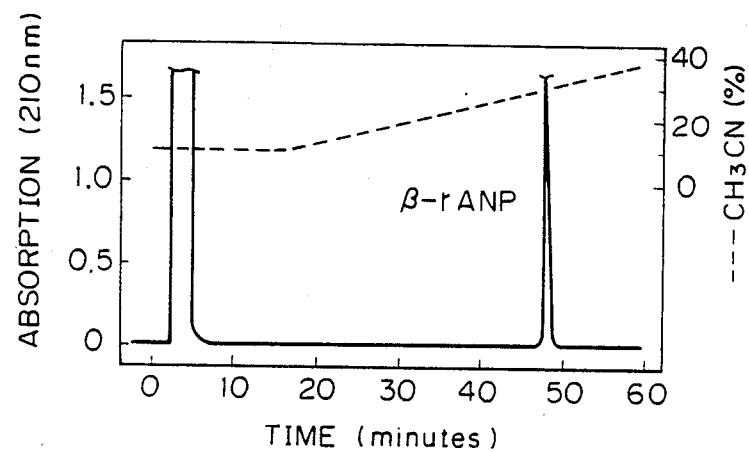
FIG. 4 is a chart showing an elution profile wherein β-rANP is finally purified by reverse phase HPLC with TSK LS-410 ODS SIL column.

The combined fraction was then subjected to cation exchange HPLC in a TSK-CM2SW column (Toyo Soda). Elution was carried out by linear gradient with (A) 10 mM ammonium formate (pH 6.6)/acetonitrile (90:10) and (B) 1.0M ammonium formate (pH 6.6)/acetonitrile (90:10), changing the concentration of formate from 10 mM to 0.75M for 140 minutes. A set of fractions (No. 58 and 59, retention time 121 to 130 minutes) with chicken rectum relaxation activity was obtained. The elution profile is shown in FIG. 3. The active fractions were combined and subjected to reverse phase HPLC in a TSK LS-410 OPS SIL column (φ4.0×250 mm, Toyo Soda). Elution was carried out with (A) water/acetonitrile/10% trifluoroacetic acid (90:10:1) and (B) water/acetonitrile/10% trifluoroacetic acid (40:60:1) as eluents wherein the eluent (A) was used for 15 minutes and then linear gradient from (A) to (B) was used for 60 minutes, at a flow rate of 1.0 ml/min. A main peak was collected and 90 n mole (468 μg) of substantially pure β-rANP was obtained. The elution profile is shown in FIG. 4.

EXAMPLE 2

Preparation of parenteral composition (A) Injection solution
Composition

| Composition | |
| --- | --- |
| β-rANP | 2 g |
| sodium chloride | 8 g |
| ascorbic acid | 2 g |
| sterile water | 1 l |

Method

β-rANP and sodium chloride were dissolved in sterile water, an ampule was filled with 5 ml of the solution, and the ampule was then sealed.

(B) Lyophilizate
Composition

| Composition | |
| --- | --- |
| β-rANP | 2 g |
| sorbitol | 20 g |

Method

β-rANP and sorbitol were dissolved in 200 ml of sterile water, a vial was filled with 1 ml of the solution, and lyophilized, and the vial was then sealed.

The composition is dissolved in 5 ml of sterile water before parenteral administration.

We claim:

1. A peptide β-rANP having the following formula:

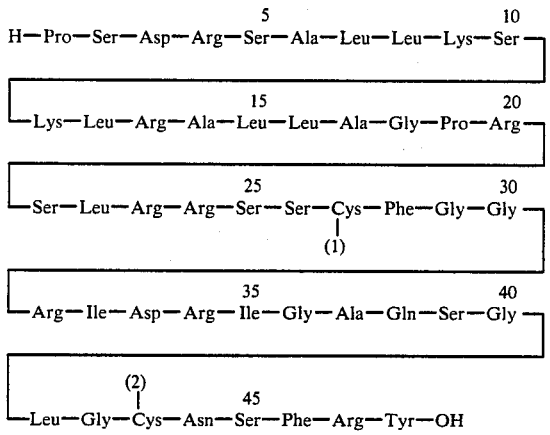

wherein (1) and (2) are bonded through a disulfide bond formed by two sulfurations of two cysteines, Pro represents L-proline, Ser represents L-serine, Asp represents L-asportic acid, Arg represents L-arginine, Ala represents L-alanine, Leu represents L-leucine, Lys represents L-lysine, Gly represents glycine, Cys represents L-cysteine, Phe represents L-phenylalanine, Ile represents L-isoleucine, Gln represents L-glutamine, Asn represents L-asparagine, and Try represents L-tyrosine, and wherein the amino acid chain has an amino-terminal at the left end and carboxy-terminal at the right end, and an acid addition salts thereof.

2. A diuretic composition containing a peptide β-rANP according to claim 1 or an acid addition salt thereof with a conventional pharmaceutical additive.

3. A diuretic composition according to claim 2, wherein the composition is a solution for parenteral administration and the conventional pharmaceutical additive is a buffer, an osmotic pressure adjusting agent or a preservative, or a combination thereof.

4. A diuretic composition according to claim 2, wherein the composition is a solution for parenteral administration and contains about 0.000005 to 5% of the β-rANP.

5. A diuretic composition according to claim 2, wherein the composition is in a lyophilized form.

6. A hypotensor composition containing a peptide β-rANP according to claim 1 or an acid addition salt thereof with a conventional pharmaceutical additive.

7. A hypotensor composition according to claim 6, wherein the composition is a solution for parenteral administration and the additive is a buffer, an osmotic pressure adjusting agent or a preservative, or a combination thereof.

8. A hypotensor composition according to claim 6, wherein the composition is a solution for parenteral administration and contains about 0.000005 to 5% of the β-rANP.

9. A hypotensor composition according to claim 6, wherein the composition is in a lyophilized form.

10. A process for the production of a peptide β-rANP or an addition salt thereof according to claim 1 which comprises the following steps:
  (a) boiling rat atrium in an acidic solution;
  (b) homogenizing said rat atrium to obtain a homogenate;
  (c) centrifuging the homegenate to obtain a supernatant containing β-rANP;
  (d) separating said β-rANP from impurities using a purification process comprising ultrafiltration, organic solvent-precipitation, adsorption chromatography, gelfiltration or high performance liquid chromatography to obtain β-rANP in substantially purified form.

11. The process according to claim 10, further comprising the step of (e) converting said β-rANP into an acid addition salt thereof or acid addition salt into free β-rANP.

12. A method of promoting diuresis comprising administering to an organism in need of such treatment a diuretically effective amount of the peptide β-rANP according to claim 1.

13. A method of lowering blood pressure comprising administering to an organism in need of such treatment an antihypertensively effective amount of the peptide β-rANP according to claim 1.

* * * * *